(12) United States Patent
Su

(10) Patent No.: US 9,173,752 B2
(45) Date of Patent: Nov. 3, 2015

(54) COIL BIOABSORBABLE BIFURCATION STENT

(75) Inventor: Shih-Horng Su, Irvine, CA (US)

(73) Assignee: Manli International Ltd., Singapore (SG)

( * ) Notice: Subject to any disclaimer, the term of this patent is extended or adjusted under 35 U.S.C. 154(b) by 209 days.

(21) Appl. No.: 13/476,336

(22) Filed: May 21, 2012

(65) Prior Publication Data

US 2013/0310920 A1 Nov. 21, 2013

(51) Int. Cl.
| | | |
|---|---|---|
| A61F 2/82 | (2013.01) | |
| A61F 2/88 | (2006.01) | |
| A61F 2/89 | (2013.01) | |
| A61F 2/06 | (2013.01) | |

(52) U.S. Cl.
CPC ... *A61F 2/88* (2013.01); *A61F 2/89* (2013.01); *A61F 2002/065* (2013.01); *A61F 2002/825* (2013.01); *A61F 2220/0041* (2013.01); *A61F 2230/001* (2013.01)

(58) Field of Classification Search
CPC .......................................................... A61F 2/82
USPC ............................................... 623/1.22, 1.35
See application file for complete search history.

(56) References Cited

U.S. PATENT DOCUMENTS

| | | | |
|---|---|---|---|
| 5,334,217 A | 8/1994 | Das | |
| 5,582,619 A | 12/1996 | Ken | |
| 5,607,445 A | 3/1997 | Summers | |
| 5,639,277 A | 6/1997 | Mariant et al. | |
| 5,643,339 A | 7/1997 | Kavteladze et al. | |
| 5,772,668 A | 6/1998 | Summers et al. | |
| 5,843,176 A | 12/1998 | Weier | |
| 6,086,611 A * | 7/2000 | Duffy et al. ................... | 623/1.35 |
| 6,162,244 A | 12/2000 | Braun et al. | |
| 6,409,750 B1 | 6/2002 | Hyodoh et al. | |
| 6,497,724 B1 | 12/2002 | Stevens et al. | |
| 6,699,279 B2 | 3/2004 | Stevens et al. | |
| 6,821,291 B2 | 11/2004 | Bolea et al. | |
| 7,048,014 B2 | 5/2006 | Hyodoh et al. | |
| 7,128,755 B2 | 10/2006 | Su et al. | |

(Continued)

FOREIGN PATENT DOCUMENTS

| | | |
|---|---|---|
| EP | 0947180 A2 | 10/1999 |
| WO | WO-02/30319 A2 | 4/2002 |
| WO | WO-2008/051579 A2 | 5/2008 |

OTHER PUBLICATIONS

Su, Shih-Horng, "New Expandable Biodegradable Polymeric Endovascular Stent Designs", The University of Texas at Arlington, Doctor of Philosophy Thesis, Chapter 2, pp. 38-49, Aug. 2000.

(Continued)

*Primary Examiner* — Thomas J Sweet
*Assistant Examiner* — Matthew Schall
(74) *Attorney, Agent, or Firm* — Cesari and McKenna, LLP

(57) ABSTRACT

A bioabsorbable, expandable coil bifurcation stent having a first, second, and third segment, in which the second and third segments are extensions of a coiled fiber in the first segment. Also disclosed is a three-segment expandable coil bifurcation stent in which the second and third segments extend from supporting fibers in the first segment. Further disclosed is an expandable bifurcation stent in which supporting fibers in the first segment also support the second and third segments. The three segments are independently adjustable to fit varied geometries.

4 Claims, 4 Drawing Sheets

(56) References Cited

U.S. PATENT DOCUMENTS

| | | |
|---|---|---|
| 7,412,993 B2 | 8/2008 | Tzeng |
| 2002/0183830 A1 | 12/2002 | Su et al. |
| 2005/0203610 A1* | 9/2005 | Tzeng .......................... 623/1.22 |
| 2005/0229998 A1 | 10/2005 | Pollock-Kueny |
| 2011/0118822 A1 | 5/2011 | Welch |

OTHER PUBLICATIONS

European Search Report, European Application No. 12187262.6-1651, Applicant: DuNing Incorporated, Date of Mailing: Feb. 21, 2013, pp. 1-9.

European Patent Office, Extended Search Report, EP Appln. No. 12195835, Feb. 21, 2013, 1 page.

* cited by examiner

COIL BIOABSORBABLE BIFURCATION STENT

BACKGROUND

A coronary bifurcation is the point at which a side-branch of a coronary artery diverges from a main branch. Approximately 15% to 20% of the 700,000 percutaneous coronary interventions performed in the U.S. during 2010 were for treating stenosis associated with a coronary bifurcation, i.e., a bifurcation lesion. Treating a bifurcation lesion, which is technically challenging, has lower procedural success rates and worse clinical outcomes as compared to treating a non-bifurcation lesion.

Typically, to treat a bifurcation lesion, a stent is implanted in the main branch but not in the side-branch, a so-called provisional approach. More specifically, the stent does not cover the opening of the side-branch, allowing for future treatment of the side-branch if necessary. This approach is taken due to the fact that routine implantation of two stents does not give superior results compared to a single stent. However, the technique frequently leaves the side-branch with significant residual stenosis.

Techniques have been developed that utilize two separate stents to treat bifurcation lesions. A major problem with these techniques is that the site at which the two separate stents overlap can disrupt blood flow and induce thrombus formation. Additionally, the use of a standard non-bioabsorbable stent typically leads to chronic foreign body reactions.

There is a need to develop a dedicated bifurcation stent that can be implanted in both the main and side-branch simultaneously, can physically support the artery walls, can elute drugs into the stenotic area to prevent restenosis, and can biodegrade over time to reduce or eliminate the occurrence of chronic foreign body reactions.

SUMMARY

The main objective of the present invention is to provide a bioabsorbable dedicated bifurcation stent having both high strength and flexibility. Such a stent can be used to treat bifurcation lesions following or in conjunction with balloon angioplasty and atherectomy, and can also be adapted to be implanted into other tissues where there is a need to physically maintain an open lumen for a specific period of time.

Thus, the main aspect of this invention relates to a bioabsorbable bifurcation stent that is convertible between a furled state and an expanded state. The bioabsorbable bifurcation stent includes three segments.

The first segment contains two parallel fibers that form a two-ply coiled fiber that is arranged into a coil structure, and also contains longitudinally disposed supporting fibers spaced around the coil structure and attached at selected points along its length. The coil structure includes central and peripheral lobes which are arranged such that, in the expanded state, the peripheral lobes merge into the central lobes, yielding a coil structure of a larger diameter as compared to the furled state.

The second and third segments both contain a coiled fiber formed into a coil structure. The coiled fiber in the second segment is the continuation of one of the two parallel fibers that make up the coiled fiber in the first segment. The coiled fiber in the third segment, on the other hand, continues from the second of the two parallel fibers in the first segment.

In another embodiment, the coiled fiber in the second segment is the continuation of a longitudinal supporting fiber that supports the coiled fiber in the first segment. The coiled fiber in the third segment, on the other hand, continues from a second longitudinal supporting fiber in the first segment.

The second and third segments, similar to the first segment, contain longitudinally disposed supporting fibers spaced around the coil structure and attached to it at selected points along its length. The coiled structure in the second and third segments also includes central and peripheral lobes. These lobes are so arranged such that, in the expanded state, the peripheral lobes merge into the central lobes, yielding a coil structure of a larger diameter as compared to the furled state. The peripheral lobes can be located inside or outside of the central lobes.

In yet another embodiment, three separate coiled fibers are joined together with two longitudinal supporting fibers. One of the longitudinal supporting fibers attached to the first coil structure is also attached to the second coiled fiber, thereby serving as a longitudinal supporting fiber in the second segment. Additionally, a second longitudinal supporting fiber in the first segment is used as one of the longitudinal supporting fibers in the third segment.

In addition to the two longitudinally disposed supporting fibers that join the three segments together, the three segments can contain additional longitudinally disposed supporting fibers spaced around the coil structure and attached to it at selected points along its length. The coiled structure in each of the three segments also includes central and peripheral lobes. These lobes are so arranged such that, in the expanded state, the peripheral lobes merge into the central lobes, yielding a coil structure of a larger diameter as compared to the furled state. The peripheral lobes can be located inside or outside of the central lobes.

All of the above-mentioned coiled fibers and reinforcing fibers are constructed of bioabsorbable polymeric material.

The details of one or more embodiments of the invention are set forth in the drawings and description below. Other features, objects, and advantages of the invention will be apparent from the description and from the claims.

DETAILED DESCRIPTION

This invention is based on the need to provide a bioabsorbable dedicated bifurcation stent having both high strength and flexibility. Such a stent can be used to treat bifurcation lesions without the long-term problems associated with currently available stents.

Figure 1:
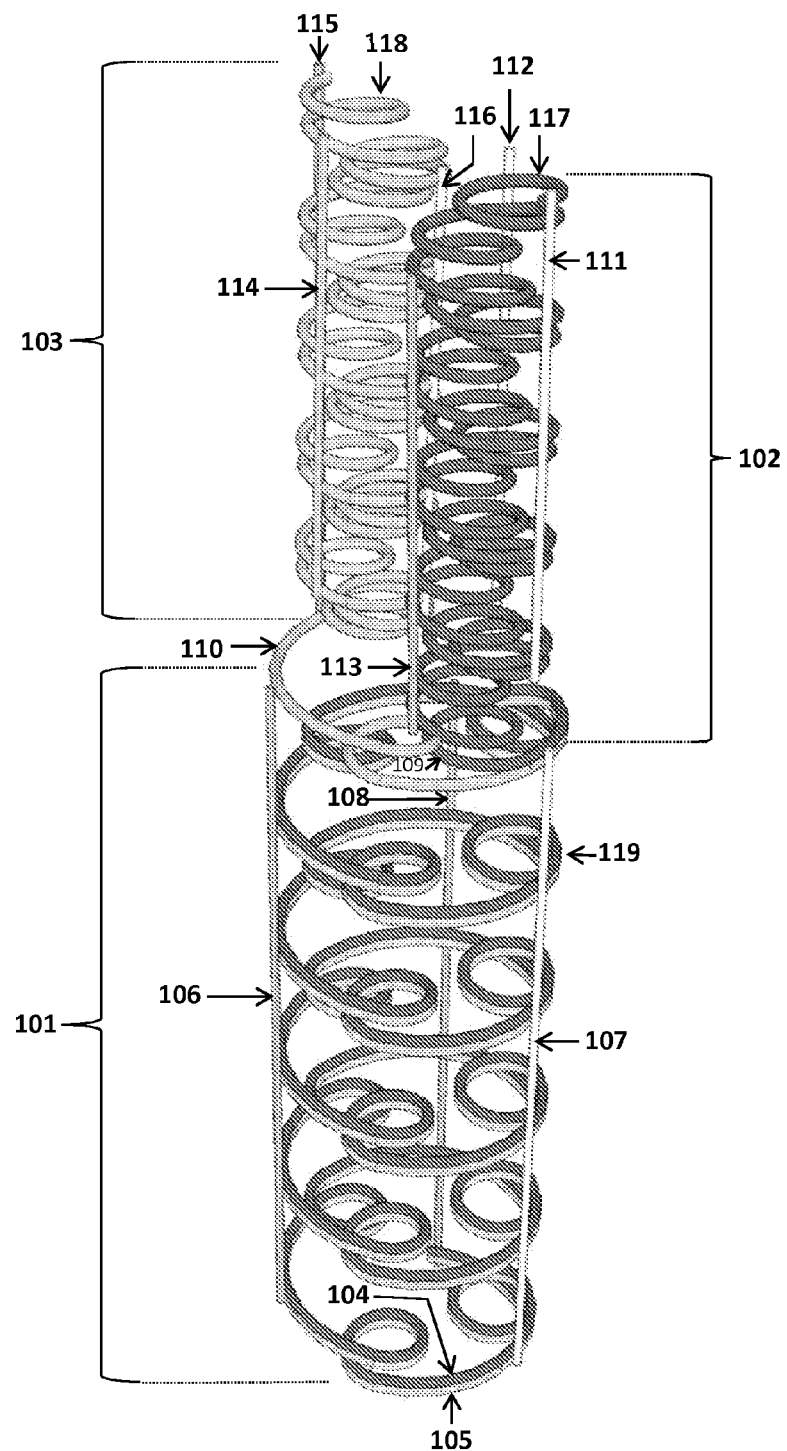
FIG. 1 is a schematic illustration of the three-dimensional structure of an expandable coil bifurcation stent according to one embodiment of the present invention.

Thus, the main aspect of this invention relates to a bioabsorbable bifurcation stent that is convertible between a furled state and an expanded state. Referring to FIG. 1, in one preferred embodiment, the bioabsorbable bifurcation stent includes three segments (101, 102, 103). The first segment (101) contains two parallel fibers (104, 105) that form a two-ply fiber (119) that is arranged into a coil structure. The second (102) and third (103) segments each contain a single fiber (117, 118) also arranged into a coil structure. The coiled fiber in the second segment (117) is the continuation of fiber (104). Fiber (105), together with fiber (104), makes up the two-ply coiled fiber (119) in the first segment (101). The coiled fiber in the third segment (118) continues from fiber (105), the second of the two parallel fibers in the first segment (101). The second and third segments are thus continuous with the first segment. A short segment of fiber (109) extends from the first segment to the second segment. This segment is flexible, allowing for the angle between the first and second segments to be easily adjusted. Another short segment of fiber (110) also extends between the first segment and the third segment. The flexibility between the segments of the bifurcation stent advantageously allows for its implantation into sites of varied geometry.

Figure 2:
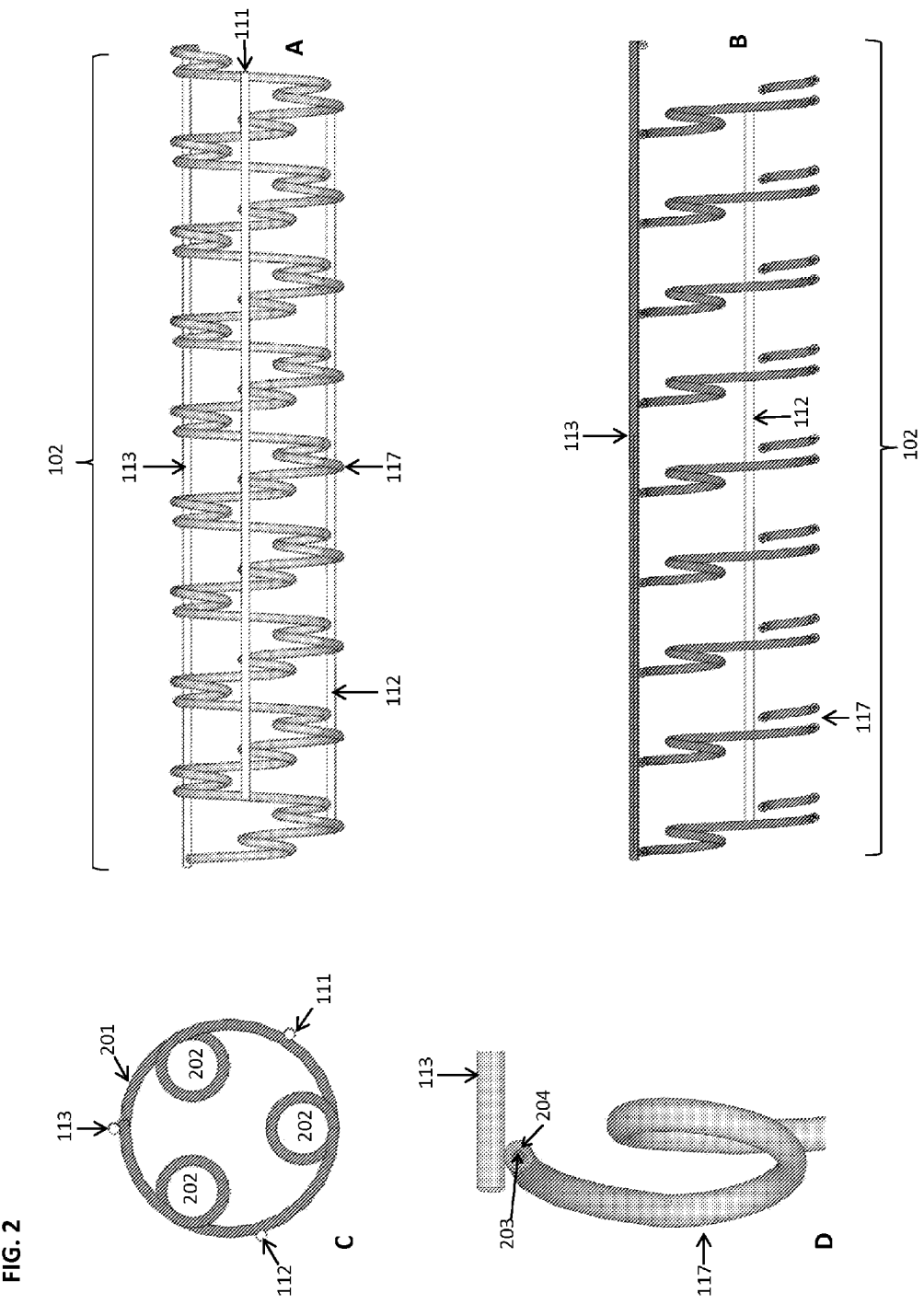
FIG. 2A, 2B, 2C, and 2D are schematic cut-away views of a single segment of a coil bifurcation stent in the furled state according to an embodiment of the invention.

A detailed view of the second segment (102) is shown in FIG. 2. The coiled fiber (117) in this segment forms a coiled structure having a central lobe (201) and three peripheral lobes (202). The peripheral lobes (202) can be inside or outside of the central lobes. These lobes are arranged such that, in the expanded state, the peripheral lobes merge into the central lobes, yielding a coil structure of a larger diameter as compared to the furled state. All three segments have a similar arrangement of central and peripheral lobes that facilitate expansion of each segment.

It is noted that any number of peripheral lobes can be incorporated into the coil structure of each segment. The number of peripheral lobes can be selected depending upon the desired increase in diameter of a segment when it transforms from the furled to expanded state. For example, a central lobe that contains 4 peripheral lobes can expand its diameter to a greater extent than a central lobe containing only 3 peripheral lobes.

Referring back to FIG. 1, together with FIG. 2, all three segments contain longitudinally disposed supporting fibers (106, 107, 108, 111, 112, 113, 114, 115, 116) spaced around their respective coil structures and are attached to them at selected points along their lengths. Like the number of peripheral lobes mentioned above, differing numbers of supporting fibers can be present in the three segments, depending upon the degree of supporting needed. Generally, the number of supporting fibers in a segment equals the number of peripheral lobes in that segment. For example, as depicted in FIG. 2C, a segment that contains three peripheral lobes (202) also has three supporting fibers (111, 112, 113). A segment that contains five peripheral lobes would have five supporting fibers.

Figure 3:
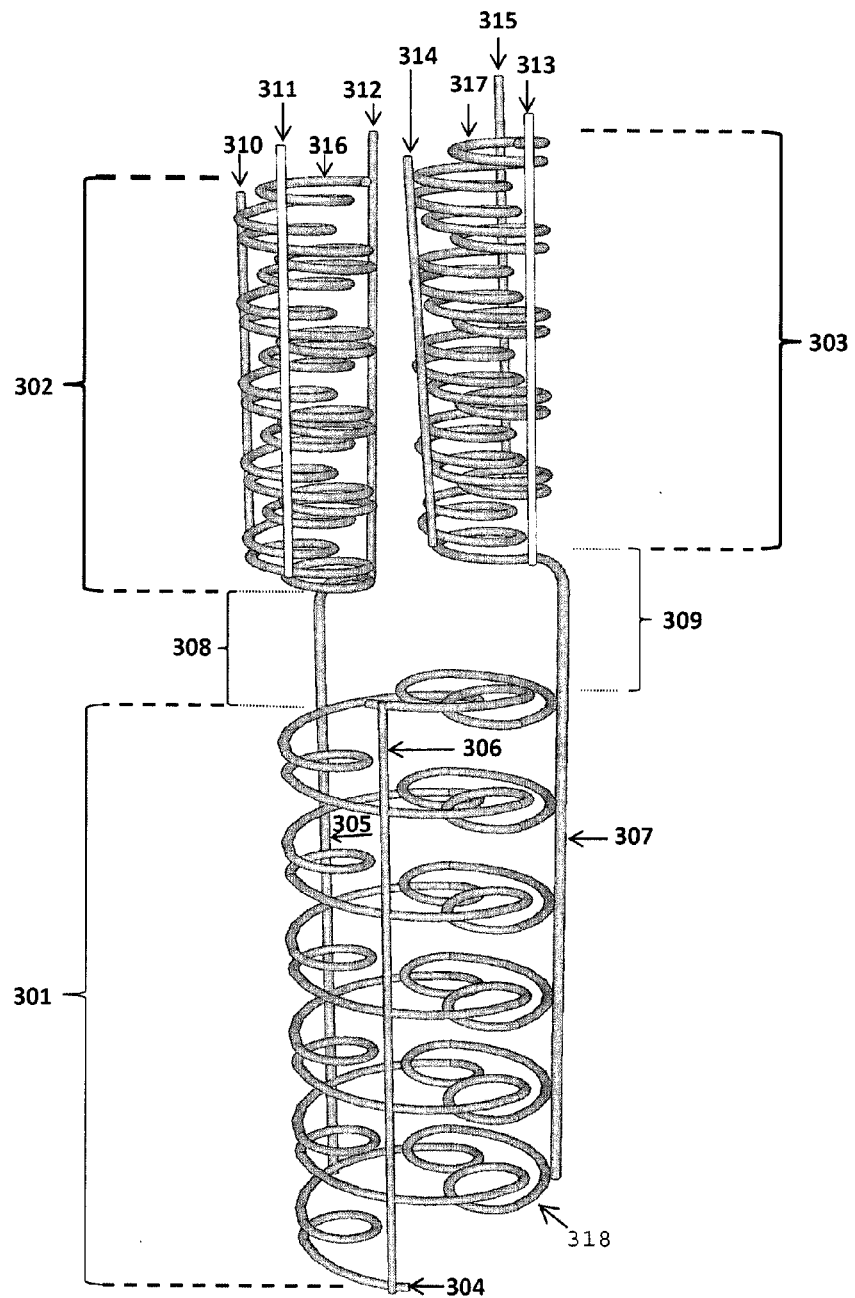
FIG. 3 is a schematic illustration of the three-dimensional structure of an alternate embodiment of an expandable coil bifurcation stent.

An alternative embodiment is depicted in FIG. 3. The first segment (301) contains a fiber (304) arranged into a coil structure (318). The coil structure (318) in the first segment (301) is supported by three longitudinal supporting fibers (305, 306, 307). The second (302) and third (303) segments each contain a single fiber (316, 317) also arranged into a coil structure. The coiled fiber in the second segment (316) is the continuation of one of the three longitudinal supporting fibers (305) in the first segment (301). The coiled fiber in the third segment (317) continues from another longitudinal supporting fiber (307) in the first segment (301). The second and third segments are thus continuous with the first segment.

Both the second and third segments include longitudinally disposed supporting fibers (310, 311, 312, 313, 314, 315) spaced around their respective coil structures and attached to them at selected points along their lengths. The number of supporting fibers can vary as described above.

A short segment of fiber (308) extends from the first segment to the second segment. This segment is flexible, allowing for the angle between the first and second segments to be easily adjusted. Another short segment of fiber (309) also extends between the first segment and the third segment. The flexibility between the segments of the bifurcation stent advantageously allows for its implantation into sites of varied geometry.

Figure 4:
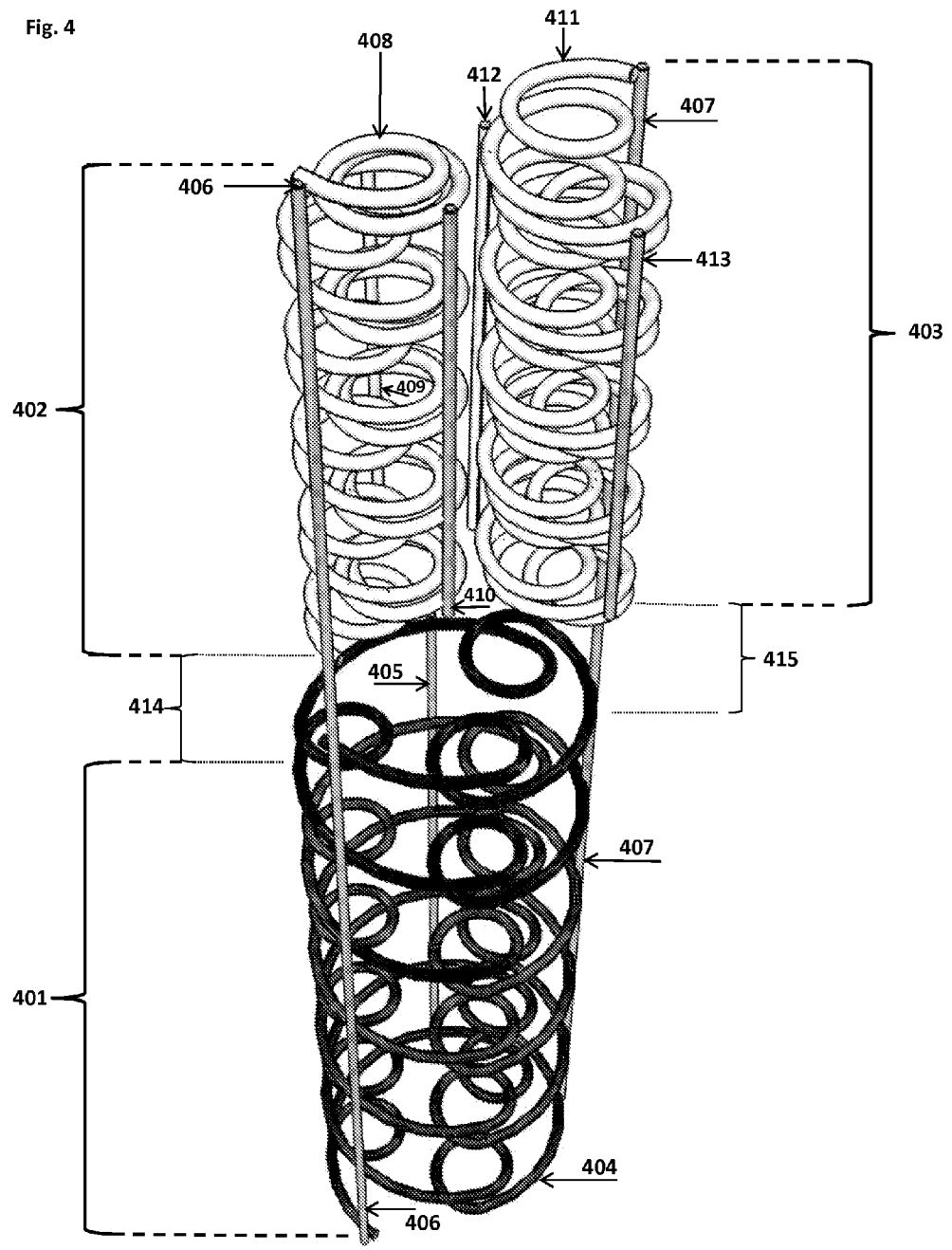
FIG. 4 is a schematic illustration of the three-dimensional structure of an additional embodiment of an expandable coil bifurcation stent.

An additional embodiment is depicted in FIG. 4. The first segment (401) contains a coiled fiber (404) and three longitudinally disposed supporting fibers (405, 406, 407). One of the three supporting fibers (406) extends beyond the first segment (401) into the second segment (402), where it also serves as a supporting fiber. The second segment also contains a coiled fiber (408) and longitudinally disposed supporting fibers (406, 409, 410). The number of supporting fibers can vary as described above.

Similarly, another supporting fiber (407) in the first segment (401) extends into the third segment (403), where it serves as a supporting fiber. The third segment (403), similar to the first (401) and second (402) segments, contains a coiled fiber (411) as well as longitudinally disposed supporting fibers (407, 412, 413). The number of supporting fibers can also vary as described above.

A short segment of fiber (414) extends from the first segment to the second segment. This segment is flexible, allowing for the angle between the first and second segments to be easily adjusted. Another short segment of fiber (415) also extends between the first segment and the third segment. The flexibility between the segments of the bifurcation stent advantageously allows for its implantation into sites of varied geometry.

The arrangement of central lobes, peripheral lobes, and supporting fibers in each of the three segments of the above-described embodiments is similar to that described in U.S. Pat. No. 7,128,755.

In one embodiment, the diameter of each coil structure is the same. In another embodiment, the diameter of each coil structure is different from one another. For example, in the expanded state of the stent, the first segment can be larger in diameter than either the second or third segment. This is advantageous for use in stenting a coronary artery bifurcation in which the main branch is larger in diameter than either branch leading from the bifurcation.

A bifurcation stent having the tripartite structure described above can be constructed in which the furled diameter of each segment is equivalent, thus facilitating implanting of the bifurcation stent via a catheter, yet, in the expanded state, each segment can have a different diameter.

As mentioned above, all three segments contain coiled fibers and supporting fibers. The diameter of the fibers or the supporting fibers can be from 0.01 mm to 2.5 mm in diameter, depending on the specific application. Additionally, the fibers, supporting fibers, or both can be solid, multi-layered, or hollow. An exemplary hollow fiber in a cut-away view is depicted in FIG. 2D. Coiled fiber (117) consists of a lumen (203) surrounded by bioabsorbable polymeric material (204).

All of the above-mentioned coiled fibers and longitudinal supporting fibers are constructed of bioabsorbable polymeric material. Examples include, but are not limited to polydioxanone, polyglycolide, polycaprolactone, polylactides, poly-L-lactide, poly-D,L-lactide, poly (L-lactide-co-glycolide), poly (D,L-lactide-co-glycolide), poly (L-lactide-co-D,L-lactide), poly (L-lactide-co-trimethylene carbonate), polyhydroxyvalerate, or ethylvinylacetate. Mixtures of two or more of the above-listed polymers can also be used to manufacture the coiled fibers.

The polymer used to make the fibers is selected depending upon the desired degradation time required for a particular application. For example, a polycaprolactone-containing fiber will degrade at a slower rate as compared to a poly D,L-lactide-containing fiber. Degradation rate is also influenced by the average molecular weight of the polymer, with polymers of higher molecular weight degrading at slower rates than polymers of lower molecular weights. Fibers having a predetermined degradation rate can be constructed by selecting a combination of specific polymer type and molecular weight.

The above-described bifurcation stent can be a drug-eluting stent. For example, drugs for the prevention of restenosis can be incorporated into the fiber material or can be added to the center of a hollow fiber used to construct the stent. In this way, the amount of drug that can be incorporated into the stent can range, for example, from 0.1 to 99.9% by weight of the bioabsorbable polymeric material used to construct the stent. Solid, multi-layered, and hollow drug-loaded fibers that can be incorporated into the inventive bifurcation stent are described in U.S. patent application Ser. No. 13/435,487.

All references cited herein are hereby incorporated by reference in their entirety.

Without further elaboration, it is believed that one skilled in the art can, based on the description above, utilize the present invention to its fullest extent. The specific examples below are to be construed as merely illustrative, and not limitative of the remainder of the disclosure in any way whatsoever.

EXAMPLE 1

Construction of a Coil Bifurcation Stent

The coil bifurcation stent was manufactured using a mandrel that contains three parts, i.e., a main mandrel and two bifurcation mandrels. Each of the two bifurcation mandrels was screwed into the end of the main mandrel to form a Y-shaped mandrel.

Construction of the stent was accomplished by first coiling a two-ply bioabsorbable fiber around the main mandrel until the end of the main mandrel where the bifurcation mandrels are screwed into was reached. Then, the two-ply fiber was split into two individual fiber plies. One individual fiber ply was coiled around one of the two bifurcation mandrels attached to the main mandrel. The other individual fiber ply was coiled around the other bifurcation mandrel.

After forming the three coiled structures, three longitudinal supporting fibers were attached to each of the three coiled structures. The longitudinal supporting fibers can be attached on either the exterior surface or the inner lumen surface of the coils.

After the longitudinal supporting fibers were attached to the coils, the coil structures were removed from the mandrels by first unscrewing the bifurcation mandrels, sliding these mandrels away from the main mandrel, and sliding the coils off of the main mandrel.

Peripheral lobes were formed by placing a hook around a coil midway between the attachment points of two longitudinal supporting fibers and rotating the hook 360°, thereby forming the peripheral lobe. This process was repeated along the entire length of all three segments, thereby forming a coil bifurcation stent. When a peripheral lobe was formed by the hook rotation, it was outside the central lobe. The peripheral lobe can be left in this position. Alternatively, it can be flipped inside the central lobe.

The peripheral lobes thus formed can be perpendicular or parallel to the center line of their corresponding segment. In use, once the bifurcation stent is crimped onto a balloon catheter, all of the peripheral lobes are in a direction parallel to the center line of the stent body.

EXAMPLE 2

Alternative Construction of a Coil Bifurcation Stent

The coil bifurcation stent was manufactured using the Y-shaped mandrel described above.

Construction of the stent was accomplished by first coiling a bioabsorbable fiber around the main mandrel until the end of the main mandrel where the bifurcation mandrels are screwed into was reached. Then, three longitudinal supporting fibers were attached to this first fiber coil. The three longitudinal support fibers can be attached on either the exterior surface or the inner lumen surface of the first fiber coil. Two of the three longitudinal supporting fibers were longer than the third longitudinal supporting fiber and extended beyond the end of the first coiled fiber. Each of the two extended longitudinal supporting fibers was then coiled around a different one of the two bifurcation mandrels to form two coiled segments.

After the long supporting fibers were wrapped around the bifurcation mandrels, longitudinal supporting fibers were attached to the two just-formed fiber coiled structures. As in the first fiber coil, the longitudinal support fibers can be attached on either the exterior surface or the inner lumen surface of the fiber coil.

The coil structures were removed from the mandrels in the manner described above.

Peripheral lobes were formed also in the manner described above. Again, the peripheral lobes can be located outside or inside of the central lobes, and can be perpendicular or parallel to the axis of their corresponding coiled segment.

EXAMPLE 3

Additional Construction Method of a Coil Bifurcation Stent

Three individual bioabsorbable fibers were each coiled around a separate mandrel to form three coiled fiber structures. Two long and one short longitudinal supporting fiber were attached to one of the three coiled structures to form a main segment. The two long supporting fibers extended beyond the end of the first coiled structure to which they were attached. One of the two long supporting fibers was attached to the second of the three coiled structures to serve as a support for the second coiled structure. The other long longitudinal fiber was attached to the third of the three coiled structures to serve as a support for the third coiled structure. Two additional short longitudinal supporting fibers were attached to each of the second and third coiled structure.

Peripheral lobes were formed also in the manner described above. Again, the peripheral lobes can be located outside or inside of the central lobes, and can be perpendicular or parallel to the axis of their corresponding coiled segment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A bioabsorbable stent convertible between a furled state and an expanded state, comprising;
   a first segment having a longitudinal axis and a circumference, the first segment containing a helically coiled fiber extending along the entire longitudinal axis of the first segment and extending around the circumference of the first segment and defining a first coil structure, and a first longitudinally disposed supporting fiber and a second longitudinally disposed supporting fiber each spaced around the first coil structure and attached at selected points along the length of the first coil structure;
   a second segment having a longitudinal axis and a circumference, the second segment containing a second helically coiled fiber extending along the entire longitudinal axis of the second segment and extending around the circumference of the second segment and defining a second coil structure, and a portion of the first longitudinally disposed supporting fiber attached at selected points along the length of the second coil structure; and
   a third segment having a longitudinal axis and a circumference, the third segment containing a third helically coiled fiber extending along the entire longitudinal axis of the third segment and extending around the circumference of the third segment and defining a third coil structure, and a portion of the second longitudinally disposed supporting fiber attached at selected points along the length of the third coil structure, wherein all of the helically coiled fibers and supporting fibers contain bioabsorbable polymeric material.

2. The bioabsorbable stent of claim 1, wherein each of the helically coiled fibers or each of the supporting fibers includes a drug.

3. The bioabsorbable stent of claim 1, wherein the bioabsorbable stent has a predetermined rate of degradation.

4. The bioabsorbable stent of claim 1, wherein the bioabsorbable polymeric material is selected from the group consisting of polydioxanone, polyglycolide, polycaprolactone, polylactides, poly-L-lactide, poly-D,L-lactide, poly (L-lactide-co-glycolide), poly (D,L-lactide-co-glycolide), poly (L-lactide-co-D,L-lactide), poly (L-lactide-co-trimethylene carbonate), polyhydroxyvalerate, and ethylvinylacetate.

* * * * *